Figure 1:
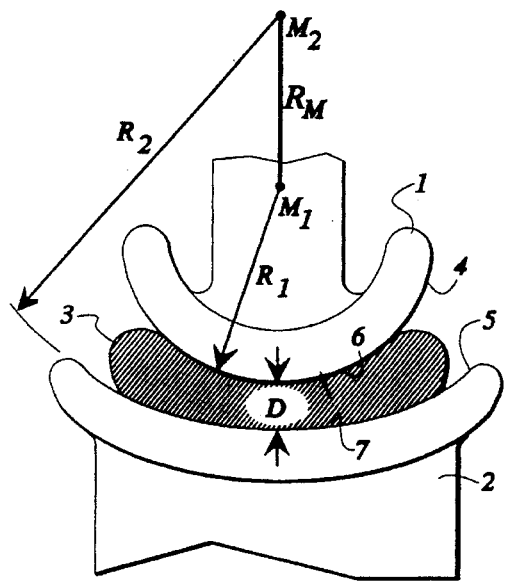

United States Patent [19]

Kubein-Meesenburg et al.

[11] Patent Number: 5,556,432
[45] Date of Patent: Sep. 17, 1996

[54] ARTIFICIAL JOINT

[75] Inventors: Dietmar Kubein-Meesenburg, Kreiensen; Hans Nagerl, Klein-Lengden, both of Germany

[73] Assignee: Joachim Theusner, Munchen, Germany

[21] Appl. No.: 15,206

[22] Filed: Feb. 9, 1993

[30] Foreign Application Priority Data

Dec. 11, 1991 [DE] Germany ............................ 41 40 837.3
Jan. 31, 1992 [DE] Germany ............................ 42 02 717.9

[51] Int. Cl.⁶ ...................................................... A61F 2/38
[52] U.S. Cl. .............................................. 623/20; 623/18
[58] Field of Search ................................... 623/20, 22, 18, 623/19

[56] References Cited

U.S. PATENT DOCUMENTS

| | | |
|---|---|---|
| Re. 29,757 | 9/1978 | Helfet . |
| 3,748,662 | 7/1973 | Helfet . |
| 3,868,730 | 3/1975 | Kaufer et al. ............................ 623/20 |
| 3,906,550 | 9/1975 | Rostoker et al. . |
| 3,916,451 | 11/1975 | Buechel . |
| 4,003,095 | 1/1977 | Gristina . |
| 4,224,696 | 9/1980 | Murray . |
| 4,293,963 | 10/1981 | Gold et al. ............................ 623/20 |
| 4,808,185 | 2/1989 | Penenberg et al. . |
| 5,064,437 | 11/1991 | Stock et al. ............................ 623/20 |
| 5,197,986 | 3/1993 | Mikhail ............................ 623/20 |

FOREIGN PATENT DOCUMENTS

| | | |
|---|---|---|
| 0498586 | 8/1992 | European Pat. Off. . |
| 3908958 | 9/1990 | Germany . |
| 2199753 | 12/1987 | United Kingdom . |
| 8704917 | 8/1987 | WIPO . |

*Primary Examiner*—Mary Beth Jones
*Assistant Examiner*—Bruce E. Snow
*Attorney, Agent, or Firm*—Jones & Askew

[57] ABSTRACT

Artificial joint, in particular an endoprothesis for the human knee joint, consisting of at least two joint parts moving with respect to each other, a joint head and a joint base, with toroidal joint surfaces, that have function surfaces with differing circular intersection contours in mutually perpendicular planes—a longitudinal plane and a transverse plane—whereby the curve ratios of the function surfaces are defined in each of the planes as either convex—convex, convex-concave, or concave—concave, and the joint geometry of the function areas to each other in each of the two planes is determined by a link chain with two link axes (dimeric link chain), which proceed through the rotation centers of the function areas with the radii of the attendant intersection contours, respectively.

10 Claims, 6 Drawing Sheets

ARTIFICIAL JOINT

The present invention pertains to an artificial joint, particularly an endoprothesis for the human knee joint, consisting of at least two joint parts with curved joint surfaces moving with respect to each other.

From the German Patent Application P 39 08 958.4 an artificial joint is already known for the replacement in particular of human joints, consisting of at least two joint parts with spherical function surfaces moving with respect to each other. The curve ratios of the function surfaces having circular intersection contour are convex—convex, convex-concave or concave—concave to each other, and the joint geometry is fixed through a link chain with two link axes (dimeric link chain), which proceed through the rotation centers of the function surfaces. Now in this case, the joint surfaces are of spherical design, so that a joint movement with five degrees of freedom is possible.

But it turns out however, that such joints are not suitable for copying special joint functions, for instance the human knee.

The task underlying the invention is to create an artificial joint, which has a freedom of movement only in one joint plane and that exhibits simultaneously a large mechanical stability with a large range of variation for adaptation to individual conditions.

According to the invention this is achieved by an artificial joint, particularly an endoprothesis for the human knee, consisting of at least two sections of a joint moving with respect to each other, said sections are a joint head and a joint base, with toroidal with circular cross-section contours joint areas, having functional surfaces in mutually perpendicular planes—a sagittal plane and a frontal plane—exhibiting differing circular intersection contours, whereby the curve ratios of the function surfaces of each of the planes is either convex—convex, convex-concave or concave—concave, and the joint geometry of the function surfaces to each other is defined in each of the two planes by a link chain with two link axes (dimeric link chain), which proceed through the rotation centers of the function surfaces of the particular, pertinent intersection contours. Now in this case it is also preferable to provide a pressure distribution body between the sections of the joint, whose slide surfaces touching the joint surface have a toroidal configuration adapted to the joint surfaces, whereby the pressure distribution element has a minimum thickness, which lies on the connecting line of the rotation centers of the function surfaces having circular intersection contours. Because of the toroidal joint surfaces provided according to the invention, there results a freedom of motion only in one of the planes, and of course, preferably in the sagittal plane, but where in the frontal plane perpendicular to this, a limited freedom of movement is present. The invention rests on the surprising finding that the joint paths of the human knee can be replaced through toroidal surfaces of the design according to the invention of the intersection contours in mutually perpendicular planes. The pressure stresses occurring in this case can be mastered through the application of appropriately solid materials. The pressure distribution element, which it is preferable to use, ensures a force and pressure-tight linking between the two joint parts and a distribution of the occurring pressure loads onto a larger area, from which a high mechanical stability emerges and makes it possible to use materials which have a smaller mechanical pressure resistance.

According to the invention it is furthermore profitable, when the function surfaces of the circular intersection contours of both planes—the sagittal and the frontal planes—are designed as convex-concave to such an extent that their rotation centers lie within the joint part, particularly a first joint head with the convex circular intersection contour, and the joint axis of the rotation centers moves along a circular path having a radius $R_M = R_2 - R_1 - D$ and/or a spacing $R_{M1} = R_{22} - R_{11} - D$, whereby $R_2$ is larger than the sum of $R_{11}$ and D and/or $R_{22}$ is greater than or equal to the sum of $R_{11}$ and D, and the rotation centers of the function areas of the frontal plane do not coincide with the rotation axes through the rotation centers of the functional areas of the sagittal plane. Hereby D=0 in the version without pressure distribution elements. The rotation centers $M_{11}$ and $M_{22}$ must not coincide. The rotation center $M_{22}$ can lie in the direction of the thigh and/or laterally toward the inside (medial) or outside (lateral) offset from the rotation center $M_{11}$. The joint designed in this manner is particularly suited as an endoprothesis for the medial joint section of the human knee. This medial section of the joint is intended to replace the natural articulation between the medial thigh (femur) and the medial shin (tibia) of the joint head. Now in this case, in the sagittal plane a turned over, pressure connected dimeric link chain is formed, which has a limited freedom of movement in the frontal plane because of the toroidal formation whereby a stable position of the sliding elements to each other will be assured under pressure stress.

Furthermore it can be expedient, according to the invention, for the functional surfaces with the circular intersection contours to have curvature relations in the one plane—the sagittal plane—such that they are formed as convex—convex, such that their rotation centers lie in the attendant part of the joint, and the path of the joint axis of the rotation centers has a radius $R_L = R_8 + R_9 + D$; also, the functional surfaces lying in the other plane—the frontal plane—have curvature relations of their circular intersection contours with the radii $R_{81}$, $R_{91}$, such that they are formed convex-concave, so that their rotation centers $M_{81}$, $M_{91}$ lie within the part of the joint with the convex intersection contour of the functional surface and the rotation centers have a spacing of $R_{L1} = R_{91} - R_{81} - D$, whereby $R_{91}$ is greater than or equal to the sum of $R_{81}$ and the minimum thickness D of the pressure distribution elements and also the rotation centers $M_{81}$ and $M_{91}$ do not coincide with the rotation axes through the rotation centers $M_8$ and $M_9$. Here again, the condition D=O applies for the configuration without pressure distribution element. The rotation centers $M_{81}$ and $M_{91}$ likewise must not coincide. The rotation center $M_{91}$ can lie in the direction of the thigh and/or to the side, inward (medial) or outward (lateral), offset from the rotation center $M_{81}$. A joint designed in this manner represents an endoprothesis for the lateral part of the joint of the human knee that is intended to replace the natural articulation between the lateral, femoral (thigh) and lateral tibial (shin) condylus. Now in this case, this joint has a nonturned over pressure connected dimeric link chain in the sagittal plane (longitudinal plane), and because of the toroidal design of the surface of the joint, it has a limited freedom of movement in the frontal plane (transverse plane).

In addition, the invention pertains to a coupling of the two joints above, namely the medial part of the joint and the lateral part of the joint, so that the femoral parts (portion of the thigh joint) and the tibial part (portion of the shin joint) are rigidly connected to each other. Now in this case, the medial part of the joint and the lateral part of the joint are positioned to each other so that their four axes of rotation run parallel to each other and the lateral part of the joint is set back with respect to the medial part of the joint in the sagittal plane (longitudinal plane). Thus according to the invention, a four-point joint will be created.

Additional favorable properties are presented in the other subclaims.

Figure 2:
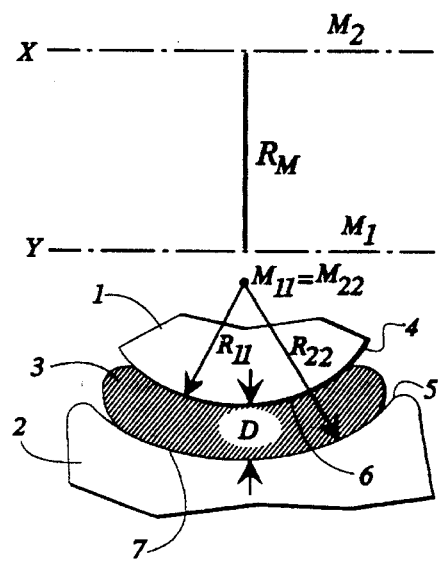
Figure 3:
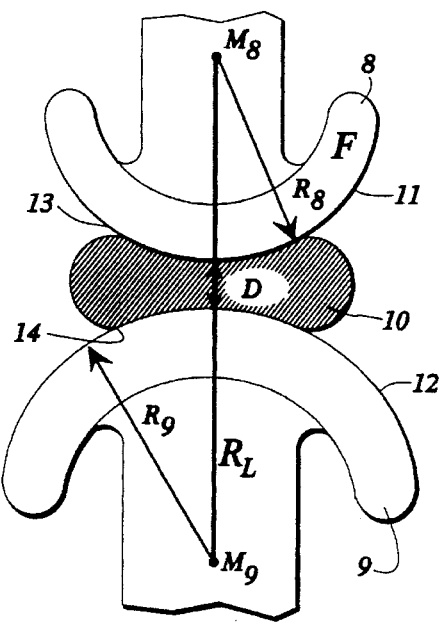
Figure 4:
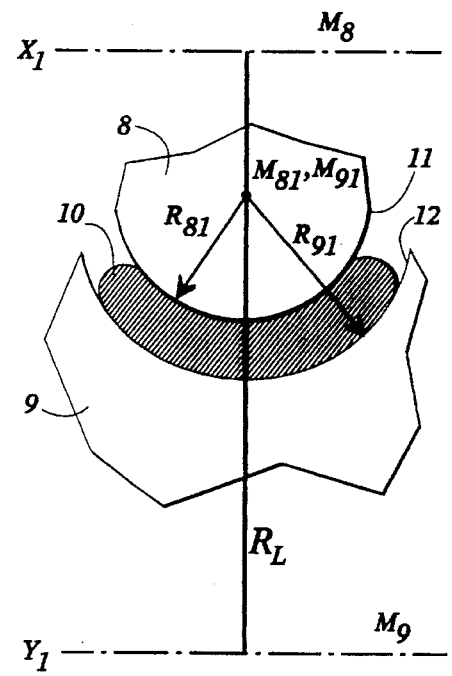
Figure 5:
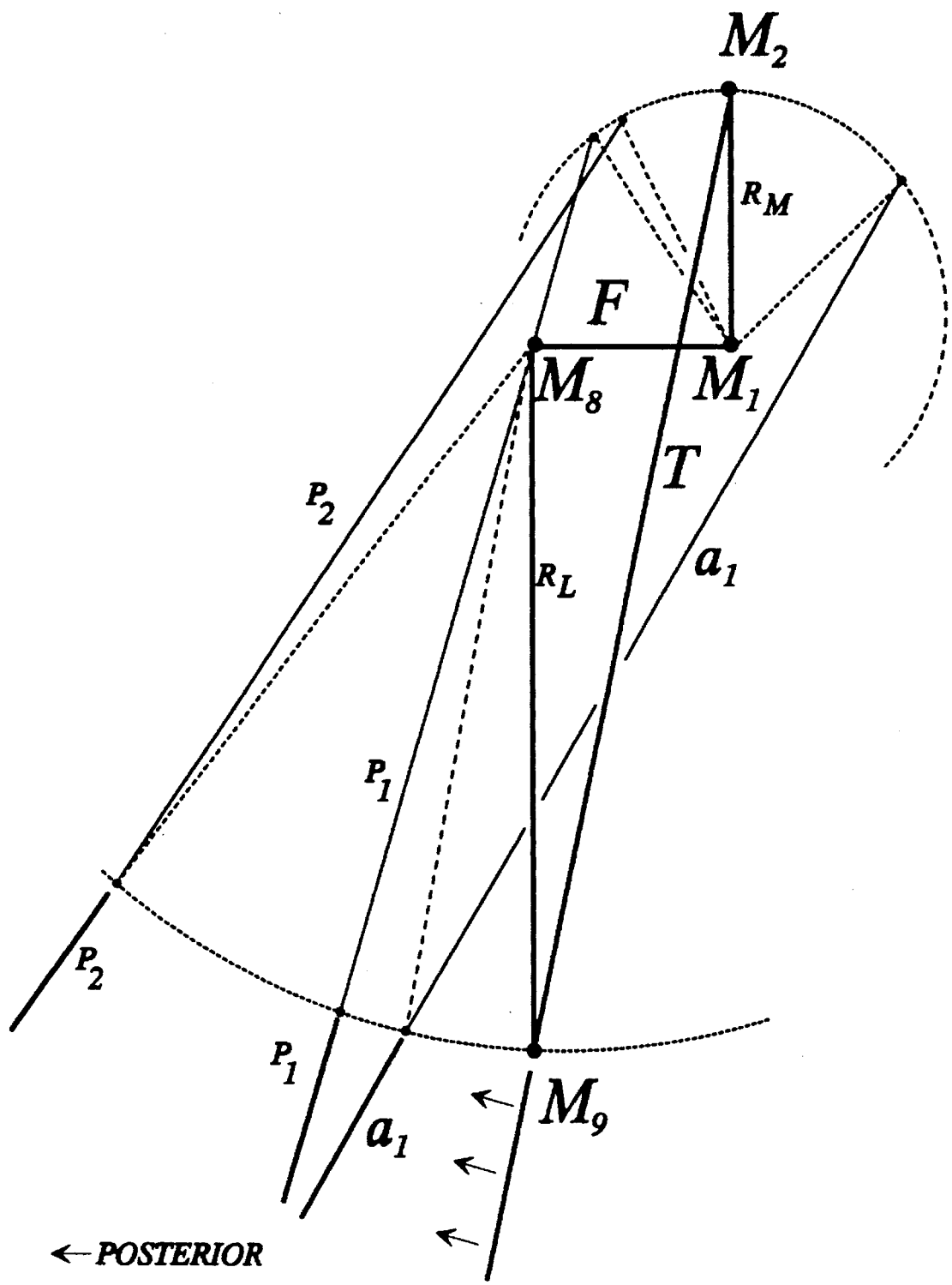
Figure 6:
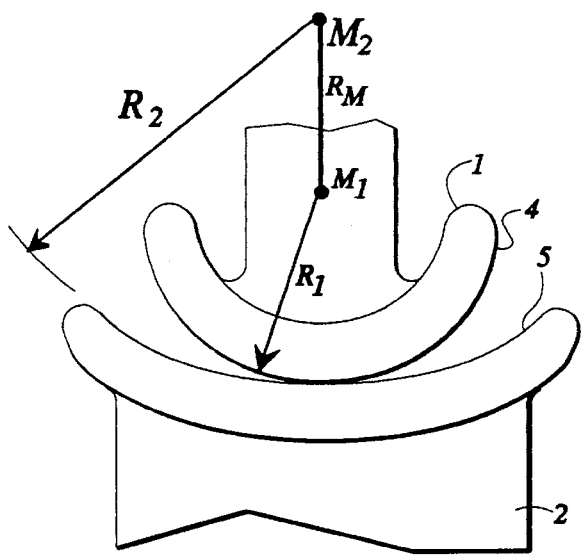
Figure 7:
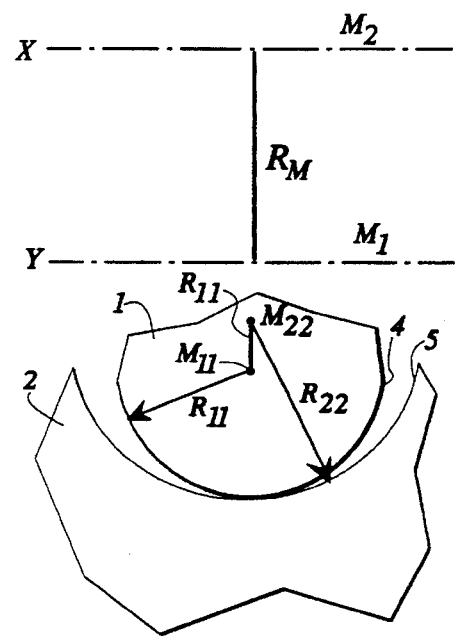
Figure 8:
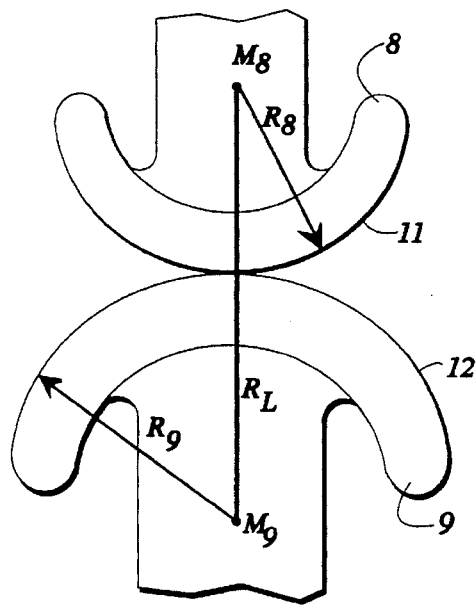
Figure 9:
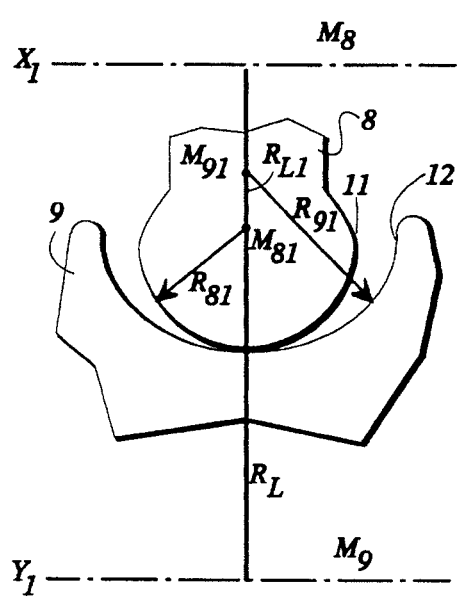
Figure 10:
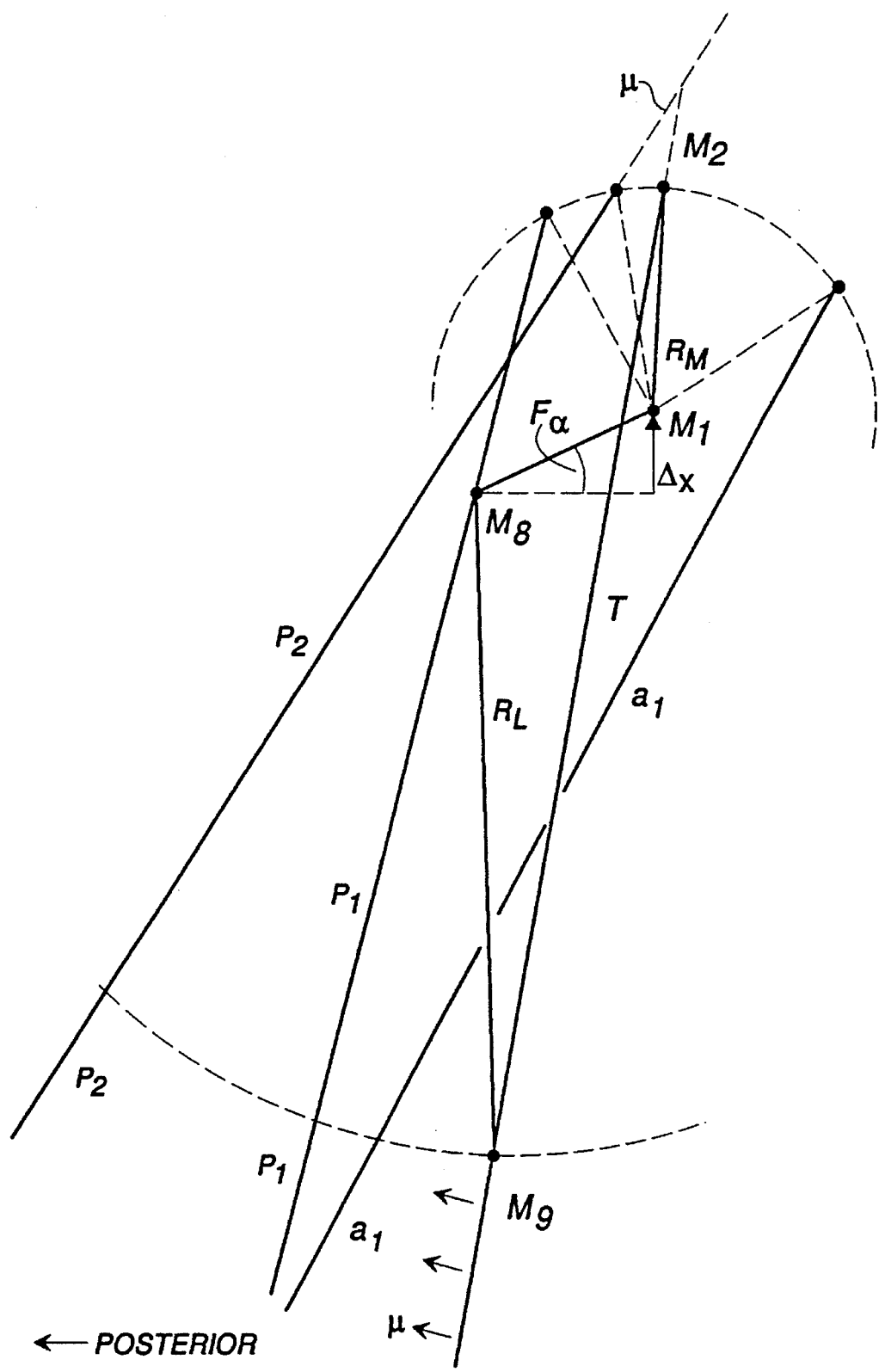
Figure 11:
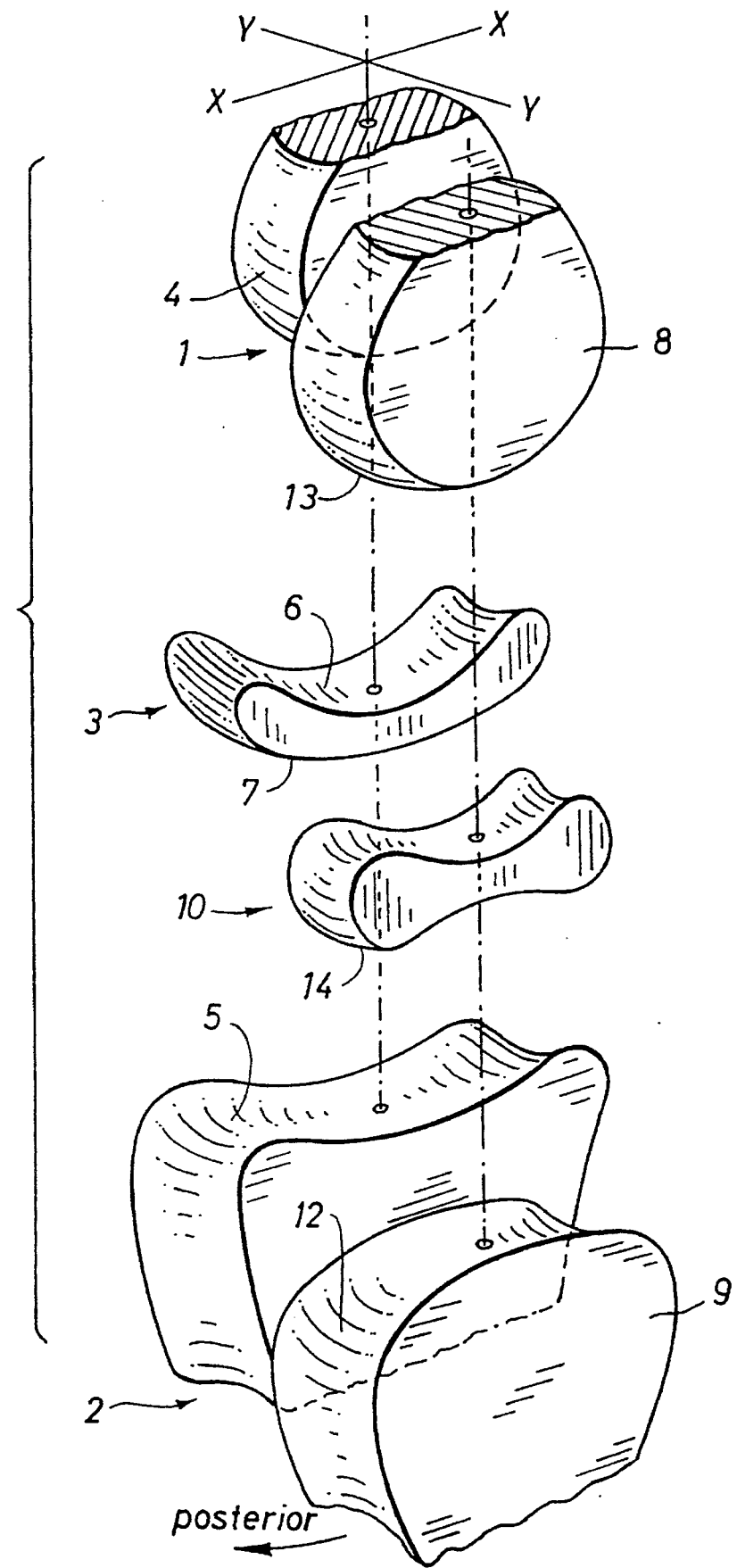
Figure 12:
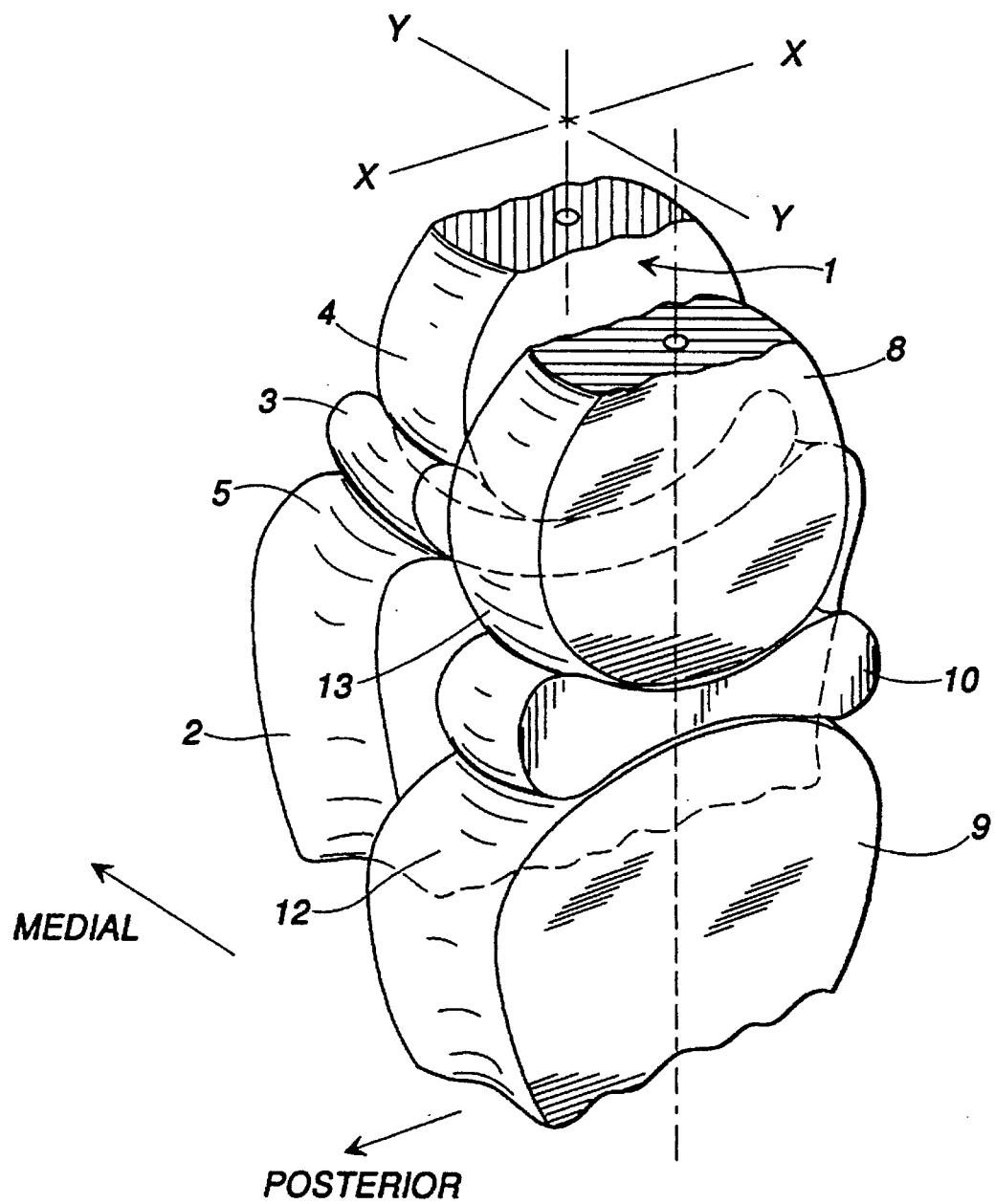

Based on the sample design contained in the attached figures, the invention will be explained in more detail. We have:

FIG. 1: A cross section in the sagittal plane (longitudinal plane) through a first-sample design of the invented joint, with pressure distribution element;

FIG. 2: A cross section through part of the joint from FIG. 1, but in the frontal plain, i.e., the transverse plane offset by 90° to FIG. 1;

FIG. 3: A cross section in the sagittal plain (longitudinal plain) through another sample design of the invented joint, with pressure distribution element;

FIG. 4: A cross section through the joint according to FIG. 3, but in the frontal plain, i.e., in a transverse plain rotated 90° to FIG. 3;

FIG. 5: A configuration of the right, human knee, showing a sagittal cross section (longitudinal cross section, side view);

FIGS. 6 & 7: Views according to FIGS. 1 and 2 through an invented joint, without pressure distribution element;

FIGS. 8 & 9: Views according to FIGS. 3 and 4 through an invented joint without pressure distribution element;

FIG. 10: A configuration of a right, human knee as per this invention, showing a sagittal cross section according to another sample design;

FIG. 11: An exploded representation, perspective view, of a joint as per this invention designed as a knee-joint replacement;

FIG. 12: The joint as per FIG. 11 shown in the assembled state.

A human knee joint consists of two joint parts; of course these are the medial part of the joint and the lateral part of the joint. FIG. 1 shows a cross section through the invented, artificial joint that serves as a replacement to the medial portion of the joint. This joint, according to the invention, is intended to replace the natural articulation between the medial femoral (upper thigh) joint head (condylus) and the medial tibial (shin bone), that is rigidly joined to the bone of the tibial condylus. Between the two parts of the joint 1 and 2, there is a pressure distribution element 3. According to the present invention, the surface 4 of the joint of joint section 1, and the surface 5 of the joint section 2, are now to be of toroidal design. For the joints 4, 5 the slide surfaces 6, 7 of the disk 3 facing the surfaces of the joints 4, 5 are accordingly of toroidal design. As is shown in FIG. 1, the part 1 of the joint in the sagittal intersection plane, i.e., in the longitudinal plane, has a function surface with circular intersection contour, whose rotation center is $M_1$ and where the circular intersection contour has a radius $R_1$. Now here, the functional surface formed in this manner has a convex shape. The part 2 of the joint likewise has a circular intersection contour, with rotation center $M_2$ and radius $R_2$, so that a concave shape results for the functional surface formed by the circular intersection contour. Now here, this type of configuration means that these rotation centers $M_1$ and $M_2$ lie within the part of the joint with the convex intersection contour, and the path of the joint axis of the rotation centers has a radius $R_M = R_2 - R_1 - D$. Now in this case, D is the minimum thickness of the disk 3 along the extension of the line connecting the two rotation centers $M_1$ and $M_2$. In this case, $R_2$ is sized so that the sum or $R_1$ and D is less than $R_2$. Thus, this configuration represents a turned over dimeric joint chain.

In FIG. 2 we see that even in the transverse plane, i.e., the frontal plain, the functional surfaces of the two parts 1, 2 of the joint have circular intersection contours, where the circular intersection contour of the functional surface of part 1 of the joint has radius $R_{11}$ and the midpoint or the rotation center $M_{11}$, and for part 2 of the joint, the functional surface has radius $R_{22}$ and midpoint $M_{22}$. Here too, the pressure distribution element 3 is seen between the two parts 1, 2 of the joint with its minimum disk thickness D. In the illustrated sample design, the midpoints $M_{11}$ and $M_{22}$ coincide. The rotation centers $M_{11}$ and $M_{22}$ must not coincide. The rotation center $M_{22}$ can be offset in the direction of the upper thigh and/or inward to the side (medial) or outward (lateral) from the rotation center $M_{11}$. However, this is merely an expedient configuration. In addition, in FIG. 2 we see how the rotation axes X, Y run through the rotation centers $M_2$ and $M_1$ in FIG. 1 within the frontal section according to FIG. 2. Notice here that the midpoints $M_{11}$ and $M_{22}$ do not coincide with the rotation axes X, Y through the midpoints $M_1$ and/or $M_2$.

FIGS. 6 and 7 present a joint corresponding to the joint in FIGS. 1 and 2 according to the invention, however without the pressure distribution element. In this case, equal parts are furnished respectively with the same reference numbers. With respect to the sizing of the geometric relations of the respective radii to each other, the condition D=O applies. Now, if one proceeds from the assumption that the radius RM is equally large at two joints according to FIGS. 1 and 2 and/or FIGS. 6 and 7, then it is expedient to enlarge $R_1$ and $R_{11}$ for the joint according to FIGS. 6, 7, with respect to the corresponding radii in FIGS. 1, 2. This measure is therefore expedient, since in this way the contact surface is as large as possible between the joint areas 5 and 6.

In FIG. 3 a cross section is presented again through the longitudinal plane and/or in the sagittal plane of a second joint according to the invention, where the lateral joint part can form a human knee joint. The lateral part of the joint replaces the natural articulation between the lateral femoral and lateral tibial condylus. The joint according to FIG. 3 is composed of the joint parts 8, 9, and of course a second joint head 8 and a second joint base 9, between which a pressure distribution element 10 is movably inserted. The joint part 8 represents thereby the femur section, which is joined rigidly with the bone of the lateral femoral condylus in the human body, and the joint part 9 represents the tibia section, which is joined rigidly with the bone of the lateral tibial condylus in the human body. The joint surfaces 11, 12 formed by the joint parts 8, 9 are designed as toroidal, so that the slide surfaces 13, 14 of the disk 10 facing the joint surfaces 11, 12, likewise are of toroidal design in adaptation to the configuration of the surfaces 11, 12 of the joint. Joint part 8 in FIG. 3 likewise has in its longitudinal plane a functional surface with a circular intersection contour, whereby this circular intersection contour has the midpoint and/or the rotation center $M_8$ and the radius $R_8$, so that a convex profile of the function area emerges. The joint part 9 has the center $M_9$ and/or the rotation center $M_9$ and has the radius $R_9$, so that likewise a convex form emerges for the arch-like intersection contour of the function area. Now, as is shown, the rotation centers $M_8$ and $M_9$, respectively, rest in the pertinent joint parts 8 and 9. The joint axis path of the rotation centers $M_8$ and $M_9$ has a radius $R_L = R_8 + R_9 + D$, whereby D is the minimum thickness of the disk 10 on the connection between the two rotation centers $M_8$ and $M_9$.

In FIG. 4 the cross section is shown according to the frontal plane and transverse plane to the display in FIG. 3. Now in this case, it is to be recognized, that also in this intersection plane, the joint elements 8, 9, respectively, have circular intersection contours of their function surfaces. The joint element 8 thus has a circular intersection contour with the center $M_{81}$ and the radius $R_{81}$, whereby a convex function surface is formed. The joint element 9 has the center $M_{91}$ and the radius whereby a concave formation of the circular intersection contour exists. Herewith the rotation centers and/or the centers $M_{81}$ and $M_{91}$ lie within the joint part 8 with the convex intersection contour of the function surface, and the joint axis path of the rotation centers $M_{81}$, $M_{91}$ is arranged to coincide in the presented sample design of the invention. The rotation centers $M_{81}$ and $M_{91}$ do not have to coincide likewise. The rotation center $M_{91}$ can lie in the direction of the upper thigh, an&or laterally to the inside (medial) or outside (lateral), displaced from the rotation center $M_{81}$. Furthermore it is to be noted that the rotation centers $M_{81}$ and $M_{91}$ do not coincide with the rotation axis $X_1$, $Y_1$ through the rotation centers $M_8$ and $M_9$. The circular-like functional surfaces in FIG. 3 represent a nonturned over pressure connected, dimeric link chain, whereby, due to the toroidal design of the surfaces of the joint, no freedom of motion exists in the frontal plain, see FIG. 4.

Essential for the flawless function of the joints per the invention according to FIGS. 1 to 4 is that the pressure distribution elements 3 and/or 10 are movable. In this case, the slide surfaces 6, 7 would have to have the smallest possible friction of the joint parts between the pressure distribution elements and the joint parts 1, 2 and/or 8, 9, and in addition, the friction force between the adjacent surfaces on both sides of the pressure distribution element must be equally large. This is achieved according to the invention since the active slide surfaces 6, 7 of the pressure distribution elements 3, 10 are the same size as the adjacent joint parts; these are the joint parts 1, 2 and/or 8, 9, respectively. The size of the respective contact surface can be achieved through the choice of the toroidal bulge radii as well as through the formation of the rim bulges of the pressure distribution elements. In addition, the slide surfaces 6, 7; 13, 14 are highly polished.

FIGS. 8 and 9 show the joint corresponding to FIGS. 3 and 4, but without pressure distribution elements. Here, again, equal parts are furnished respectively with the same reference numbers. With regard to the geometric relations of the respective radii to each other, the condition D=O applies here. Now if one proceeds from the assumption that the radius RL is equally large for two joints according to FIGS. 3, 4 and FIGS. 8, 9, then it is expedient to choose $R_8$ and $R_{81}$ larger, according to FIGS. 6 and 7, than for the joint of FIGS. 3 and 4. Due to this choice, the contact surface between the joint surfaces 11, 12 becomes as large as possible.

FIG. 5 shows schematically the structure of a right knee in the sagittal cross section with a side view; here we see the first joint according to FIGS. 1, 2 and/or FIGS. 6, 7, and the second joint according to FIGS. 3, 4 and/or FIGS. 8, 9. Now here, the individual joint parts are connected together to such an extent that the femoral first and second joint head 1, 8, and the tibial first and second joint base 2, 9, are joined together rigidly. These rigid combinations can be established by means of the femoral bone and the tibia bones themselves; they can, however, also be attained artificially, after severe bone damage, through rigid combinations. The two joints from the joint parts 1, 2 and/or 8, 9 are installed according to the invention so that their four rotation axes X, Y and $X_1$ and $Y_1$ proceed through the rotation centers $M_1$ and $M_2$ and/or $M_8$ and $M_9$ parallel to each other in two parallel planes and so that the second joint is displaced from the joint parts 8, 9 somewhat to the posterior, i.e., to the rear, compared to the first joint made up of joint parts 1, 2. A joint formation of this type represents a four-part joint, whereby the joint part marked in FIG. 5 with F is joined with the femur, and the joint part denoted by T is joined with the tibia. In the coordinate system the femur F is the pedestal, T is the link, $R_L$ and $R_M$ are the rotary links. The relative motion of the tibia opposite the femur is therefore presented as a movement of the link T. Since the length of T is larger than the sum of $R_M + R_L$, the axis $M_8$ can move out from the thickly drawn initial setting only to the posterior. The axis $M_2$ can move both to the anterior and to the posterior. But in two cases the distal extension of T, the lower thigh, pivots backward. Both cases represent two possible motions of a bending knee, where each individual motion necessarily takes place by itself. For the anterior movement of the rotation axis $M_2$, this axis moves farther to the anterior position after the anterior dead position is exceeded ($R_M$ and T form a straight line and coincide). The tibia can then assume the position $a_1$, shown as a thin line in the drawing. For the posterior motion of $M_2$, this axis reaches its most posterior position in the posterior dead position ($R_L$ and T form a straight line and coincide, position designated as $p_1$). As a result of the further movement, $M_2$ migrates then in an anterior direction. This motion happens so slowly, that after this additional pivoting of the tibia (Tibia T), the rotation axis $M_2$ appears to persist at its location (location $P_2$ Of the tibia). In each case ($a_1$, $P_1$, $P_2$) the tibia has pivoted to the rear. The artificial joint is constructed therefore so that under the effect of force connected, compressive forces, the tibia can only pivot to the rear.

Furthermore, it is possible to reduce the minimum thickness of the pressure distribution elements to zero, so that an annular ring-pressure distribution element is obtained with a central opening.

FIG. 10 shows another configuration of a joint as per this invention, presented as illustrated in FIG. 5. This configuration of the joint to replace the human knee joint shows that the first joint is composed of joint components 1, 2 and is positioned medially with respect to the laterally positioned joint made up of joint components 8, 9, and is offset by the value $\Delta x$ in the direction of the femur, with respect to its joint midpoints $M_1$, $M_2$. Due to the size of this offset, the maximum swing angle $\mu_{max}$ of the joint—which corresponds to the maximum bending angle of the human knee—will be affected to the posterior. Now in this case there is a physical necessity that the larger the femoral offset $\Delta x$, the smaller the maximum swing angle $\mu_{max}$. Preferably, the femoral offset $\Delta x$ will be selected so that the connecting path F from $M_8$ to $M_1$ will enclose an angle $\alpha$ with respect to the horizontal line, which lies between 0° and 45°: $0<\alpha<45°$. Furthermore, it is within the framework of the present invention to position the components 1, 2 or 8, 9 of the joint as per this invention such that the planes through the connecting elements $R_L$ and $R_M$ are inclined spatially to each other, so that a spherical motion will be obtained.

FIGS. 11 and 12 show a perspective view of a knee joint as per this invention, according to the sample design described in FIG. 10. Now here we see that the medial-positioned joint, composed of joint components 1, 2, 3, is offset to the posterior with respect to the lateral positioned joint, composed of joint components 8, 9, 10, and in addition, it is offset in the direction of the femur with respect to its joint midpoints. From this illustration one can see that the joint head 1 has a convex, curved functional surface 4 in both planes, that is, both in the longitudinal plane X—X, as well as in the transverse plane Y—Y. As an adaptation to this, the facing functional surface 6 of the pressure distribution element 3 has a concave curvature when viewed in the two planes X—X, Y—Y. The functional surface 5 of the joint socket 2 is curved concave in both planes X—X, Y—Y, and the functional surface 7 of the pressure distribution element 3 facing it is adapted to it and is of convex shape when viewed in both planes. The joint head 8 of the lateral joint has a function surface 11 which has a convex curvature in both planes X—X and Y—Y. Accordingly, the functional surface 13 of the pressure distribution element 10 facing this functional surface is of concave design when viewed in both planes. The joint socket 9 of the laterally positioned joint has a functional surface 12 that has a convex curvature in the longitudinal plane X—X, but in the transverse plane Y—Y it has a concave curvature. Now adapted to this, the functional surface 14 of the appurtenant pressure distribution element 10, viewed in the longitudinal plane X—X, has a concave curvature and in the transverse plane Y—Y, it has a convex curvature. The joint heads 1, 8 and the joint sockets 2, 9 are each rigidly connected to each other.

We claim:

1. An endoprosthesis for the human knee joint, comprising:

a first prosthetic joint consisting of a first joint head (1) and a first socket (2), and a second prosthetic joint consisting of a second joint head (8) and a second socket (9); wherein the prosthetic joints are arranged in parallel to each other in such a manner that the respective rotational axes (X, Y,/X1, Y1) of both joints are parallel to each other and the second prosthetic joint is shifted to the back with respect to the first prosthetic joint in the sagittal plan;

the joint heads (1, 8) are connected rigidly to each other, and the sockets (2, 9) are connected rigidly to each other;

the joint heads (1, 8) and the sockets (2, 9) have longitudinal surface areas that are surface segments of a toms and that have functional surface areas in sagittal and frontal planes that are perpendicular with respect to each other, the functional planes presenting in each one of the individual planes a single circular cross section contour with constant radius;

the functional surface areas, with circular cross section contours, of the joint head and socket (1, 2) of the first prosthetic joint, in both planes, are shaped in a convex-concave shape, and the circular cross section contours of the functional surfaces of the joint head and socket (8, 9) of the second prosthetic joint are shaped in a convex—convex shape with radii ($R_8$, $R_9$) in the sagittal plane and are shaped in a convex-concave shape with radii ($R_{81}$, $R_{91}$) in the frontal plane; and the joint geometry of the functional surface areas with respect to each other is determined in each of the two planes by a joint chain with two joint axes ($M_1$, $M_2$, $M_{11}$, $M_{22}$; $M_8$, $M_9$, $M_{81}$, $M_{91}$) of the functional surfaces with the radii ($R_1$, $R_2$, $R_{11}$, $R_{22}$, $R_8$, $R_9$, $R_{81}$, $R_{91}$) of the associated cross-section contours.

2. A joint according to claim 1, characterized by the fact that a separate pressure distribution element (3,10) rests between the surfaces (4, 5; 11, 12) of head and socket of the first and second joints, each pressure distribution element having sliding surfaces (6, 7; 13, 14) in contact with the surface of the joint and having a circular cross-section contour adapted to the surface of the joint, and the pressure distribution element (3, 10) has a minimum thickness that lies on the line connecting the rotation centers of the functional surfaces having the circular intersection contours.

3. A joint according to claim 1 or 2, characterized by the fact that function surfaces of the first joint head and first socket (1, 2) of the joint having circular cross-section contours are designed in the sagittal plane and the frontal plane as convex-concave such that their rotation centers ($M_1$, $M_2$) lie within the joint head of the joint, with the convex circular intersection contour;

the joint axis path of the rotation centers has a radius $R_M = R_2 - R_1$ respectively a distance $R_{M1} = R_{22} - R_{11}$ without pressure distribution element, or $R_M = R_2 - R_1 - D$, respectively a distance $R_{M1} = R_{22} - R_{11} - D$ with pressure distribution element, whereby $R_2$ or $R_{22}$ is greater than or equal to the sum of $R_1$ or $R_{11}$; and the minimum thickness D of the pressure distribution element, where D=O is the case without a pressure distribution element, and the rotation centers ($M_{11}$, $M_{22}$) of the functional surfaces of the frontal plane do not coincide with the rotation axes (X, Y) through the rotation centers ($M_1$, $M_2$) of the functional surfaces of the sagittal plane.

4. A joint according to claim 3, characterized by the fact that the rotation centers $M_{11}$ and $M_{22}$ coincide or differ from each other, such that the rotation center $M_{22}$ is offset in the direction of the upper thigh or inward medial to the side or outward lateral from the rotation center $M_{11}$.

5. A joint according to claim 1, characterized by the fact that the circular intersection contours of the functional surfaces of the second joint head and second socket (8, 9) of the joint comprise a joint head (8) and a joint base (9) with radii ($R_8$, $R_9$) are formed in the sagittal plane convex—convex such that their rotation centers ($M_8$, $M_9$) lie in a particular allocated part (8, 9) of the joint;

the path of the joint axis of the rotation centers ($M_8$, $M_9$) has a radius $R_L = R_8 + R_9$ and $R_L = R_8 + R_9 + D$ with pressure distribution element; and in the frontal transverse plane the curvature conditions of the circular intersection contours are designed with the radii $R_{81}$, $R_{91}$ convex-concave so that their rotation centers ($M_{81}$, $M_{91}$) lie within the part (8) of the joint with the convex intersection contour of the functional surface;

the distance of the rotation centers $R_{L1} = R_{91} - R_{81}$ and $R_{L1} = R_{91} - R_{81} - D$ with pressure distribution element, whereby $R_{91}$ is greater than or equal to the sum of $R_{81} + D$; and the minimum thickness of the pressure distribution element, where D=O is the case without pressure distribution element and also the rotation centers ($M_{81}$, $M_{91}$) do not coincide with the rotation axes ($X_1$, $Y_1$) through the rotation centers ($M_8$, $M_9$).

6. A joint according to claim 5, characterized by the fact that the rotation centers $M_{81}$ and $M_{91}$ coincide or are located apart, such that the rotation center $M_{91}$ is offset in the direction of the upper thigh or to the side, medial or lateral from rotation center $M_{81}$.

7. A joint according to claim 2, characterized by the fact that the two sliding surfaces (5, 6; 13, 14) of the pressure distribution element (3, 10) are of the same size.

8. A joint according to claim 2, characterized by the fact that the minimum thickness (D) of the pressure distribution element is zero.

9. A joint according to claim 1, characterized by the fact that the first joint made up of the first joint head and first socket (1, 2) is positioned medially and the second joint made up of the second joint head and second socket (8, 9) is positioned laterally, and that the midpoints $M_1$, $M_2$ of the lateral joint (1, 2) are offset by an amount $\Delta x$ in the direction of the femur so that the connecting path F from a rotation center $M_8$ to $M_1$ encloses an angle $\alpha$ with respect to the horizontal line that lies between 0° and 45°:0<$\alpha$<45°.

10. A joint according to claim 9, characterized by the fact that connecting elements $R_L$ and $R_M$ of the joint made up of joint components (8, 9 and 1, 2) are positioned so that the planes through the connecting elements are spatially inclined to each other.

* * * * *

UNITED STATES PATENT AND TRADEMARK OFFICE
CERTIFICATE OF CORRECTION

PATENT NO. : 5,556,432
DATED : September 17, 1996
INVENTOR(S) : KUBEIN-MEESENBURG, ET AL It is certified that error appears in the above-indentified patent and that said Letters Patent is hereby corrected as shown below:

On the title page: Item [63] Continuation should read --This is a continuation-in-part of Application No. 07/850,139 filed March 12, 1992 and now abandoned. --

In column 7, line 24, "toms" should be --torus--.

Signed and Sealed this

First Day of April, 1997

Attest:

BRUCE LEHMAN

Attesting Officer

Commissioner of Patents and Trademarks